(12) United States Patent
Levin et al.

(10) Patent No.: US 7,693,323 B2
(45) Date of Patent: Apr. 6, 2010

(54) MULTI-DETECTOR DEFECT DETECTION SYSTEM AND A METHOD FOR DETECTING DEFECTS

(75) Inventors: Evgeni Levin, Rehovot (IL); Daniel Some, Ashdod (IL); Mirta Perlman, Moshave Bet Elazari (IL)

(73) Assignee: Applied Materials, Inc., Santa Clara, CA (US)

( * ) Notice: Subject to any disclaimer, the term of this patent is extended or adjusted under 35 U.S.C. 154(b) by 1262 days.

(21) Appl. No.: 10/097,442

(22) Filed: Mar. 12, 2002

(65) Prior Publication Data

US 2003/0174878 A1 Sep. 18, 2003

(51) Int. Cl.
G06K 9/00 (2006.01)

(52) U.S. Cl. ........................ 382/142; 382/144; 382/145; 382/147

(58) Field of Classification Search ......... 382/141–152; 348/14, 16; 356/237.1, 237.2, 237.3, 237.4, 356/237.5
See application file for complete search history.

(56) References Cited

U.S. PATENT DOCUMENTS

| | | | | |
|---|---|---|---|---|
| 5,699,447 A | * | 12/1997 | Alumot et al. | .............. 382/145 |
| 5,808,735 A | | 9/1998 | Lee et al. | |
| 6,178,257 B1 | | 1/2001 | Alumot et al. | |
| 6,208,750 B1 | * | 3/2001 | Tsadka | ........................ 382/145 |
| 6,256,093 B1 | | 7/2001 | Ravid et al. | |
| 6,483,938 B1 | * | 11/2002 | Hennessey et al. | .......... 382/149 |
| 2003/0099392 A1 | | 5/2003 | Levin et al. | |

FOREIGN PATENT DOCUMENTS

WO   WO 99/67626        12/1999
WO   WO 03/078987 A1    9/2003

OTHER PUBLICATIONS

Japanese Office Action issued in Japanese Patent Application No. JP 2003-576945, dated Dec. 2, 2008.
Chinese Office Action, with English Translation, Issued in Chinese Patent Application No. CN 03808791.X dated on May 9, 2008.

* cited by examiner

*Primary Examiner*—Brian Q Le
(74) *Attorney, Agent, or Firm*—McDermott Will & Emery

(57) ABSTRACT

A method for inspecting a substrate for defects, including: A method for inspecting a substrate for defects, the method including the steps of: (i) obtaining at least two wafer element detection signal; each wafer element detection signal reflects light scattered to a distinct direction; each wafer element detection signal having a wafer element detection value; (ii) calculating at least one wafer element attribute value in response to the at least two wafer element detection signals; retrieving at least one reference wafer element attribute value, each wafer element attribute value corresponding to a reference wafer element attribute value; and (iii) determining a relationship between the at least one reference wafer element attribute value, wafer element attribute value and at least one threshold to indicate a presence of a defect.

8 Claims, 9 Drawing Sheets

MULTI-DETECTOR DEFECT DETECTION SYSTEM AND A METHOD FOR DETECTING DEFECTS

FIELD OF THE INVENTION

The present invention relates to multi-detector defect detection system and a method for detecting defects, especially for detection of defects of semiconductor devices.

BACKGROUND ART

Current demands for high density and performance associated with ultra large-scale integration require sub-micron features, increased transistor and circuit speeds and improved reliability. Such demands require formation of device features with high precision and uniformity, which in turn necessitates careful process monitoring, including frequent and detailed inspections of the devices while they are still in the form of semiconductor wafers.

Conventional in-process monitoring techniques employ a two-phase "inspection and review" procedure. During the first phase the surface of the wafer is inspected at high-speed and relatively low-resolution. The purpose of the first phase is to produce a defect map showing suspected locations on the wafer having a high probability of a defect. During the second phase the suspected locations are more thoroughly analyzed. The two-phases of the detection procedure may be implemented by the same defect detection system, but this is not necessarily so.

The two-phased inspection tool may have a single detector or multiple detectors. A multiple detector two-phase inspection device is described in U.S. Pat. Nos. 5,699,447, 5,982,921 and 6,178,257B1 of Alumot (hereinafter collectively referred to as the Alumot system) whose contents are hereby incorporated herein by reference.

The Alumot system has multiple channels for detecting defects. These multiple channels include a plurality of detectors arranged in a circular array around an objective lens.

During the first phase (also referred to as the inspection phase) each channel (a) obtains an inspected pixel, neighborhood inspected pixels, a reference pixel, and neighborhood reference pixels, (b) determines the type of the inspected pixel and/or determines the reference pixel type, (c) compares the inspected pixel and the reference pixel and a threshold that depends upon the inspected and reference pixel types, (d) and determines the presence of a defect in response to said comparison.

The step of determining the type of a pixel involves a first stage of determining the following parameters: (i) local maximum—whether the pixel is a local maximum (if the pixel is a maximum relative to his neighbors), (ii) intensity—if the pixel is intense (if the intensity of the pixel is above a threshold), (iii) ratio—if the ratio between the intensity of a pixel and the intensity of its neighbors is above a threshold and (iv) gradient—whether the pixel is located in a slope area, as determined by the gradient relative to a threshold. The second stage involves classifying the pixel as one of the following types, in response to the parameters: (I) isolated peak (if the pixel is a local maximum with significant intensity and ratio), (II) multi-peak (if the pixel is not an isolated peak, it has significant intensity and none of its neighbors is an isolated peak), (III) slope—if either one of the pixel's neighbors is an isolated peak or has above-threshold gradient, or (IV) background—if the pixel has intensity and gradient below some thresholds and none of its neighbors is an isolated peak.

The outputs (alarm values) of the multiple channels are provided to a decision table that makes a decision regarding a presence of a defect in response to the alarm values. There are three possible alarm values indicating no alarm, low alarm and high alarm.

The decision table outputs a defect flag if (i) at least one out of the eight alarm values is high alarm, and (ii) at least two alarm values from adjacent channels are either low alarm or high alarm.

In the Alumot invention and in similar inspection systems, defect detection takes place in each channel independently: both the typing process and the die-to-die comparison process are performed separately on each data stream. At most the alarm values of suspected defects from each channel are then further processed to minimize false alarms and increase reliability of defect reporting.

It is known in the art that many defects, such as foreign particles, recesses, scratches and shorts can be characterized by their scattering patterns. A light beam that is directed to a defect may be scattered to at least one direction thus defining a scattering pattern. The scattering pattern is at least partially detected by multiple detectors that are arranged in distinct angular locations around the light beam axis. It is noted that the scattering pattern is responsive to various parameters such as, but not limited to, the shape of the defect, the orientation of the defect and the like.

There is a need to provide an improved system and method for defect detection that makes use of the information collected in the different channels in a more sophisticated manner than independent typing and comparison.

There is a need to provide a system and method for defect detection that utilizes signals from multiple collection channels to compare scattering patterns, as well as multi-channel typing and high-speed defect detection.

There is a need to provide a high reliability ultra fast defect detection system and method. There exists a further need for a method for inspecting a substrate that allows a dynamic definition of pixel types.

SUMMARY OF THE INVENTION

The following terms and abbreviations shall have the following meaning throughout this specification:

Wafer Element—A relatively very small portion of an inspected wafer that is illuminated by a light beam. The wafer element is usually defined by the cross section of the impinging light beam. It is noted that the distance between adjacent wafer elements is responsive to the scanning path of the wafers, and especially to (a) the distance between adjacent scanning paths and (b) to a relationship between the scanning velocity of the wafer and the sampling rate of the detectors. Raster scan patterns and spiral scan patterns may be utilized but this is not necessarily so.

Wafer element detection signal set—(DSS)—multiple detection signals generated by multiple detectors, in response to light scattered or reflected from the wafer element to a plurality of directions. A single wafer element detection signal is denoted DS. Each DS has a wafer element detection value (DV).

Wafer Element Attribute Value—(AV)—the result of applying an attribute operator on at least two DS that belong to the same DSS. According to an aspect of the invention at least two attribute operators may be applied on at least two DSs to provide at least two AVs. An attribute operator is typically a mathematical function applied to the DSs.

Wafer element neighborhood—(N)—a neighborhood of a certain wafer element is the wafer elements that are located within a neighboring pattern around that certain wafer element. Each neighborhood wafer element has its own set (NSS) of neighborhood detection signals (NS).

Wafer element neighborhood detection signal group—(NDG)—a collection of wafer element detection signal sets of each wafer element within the neighborhood pattern.

Wafer element neighborhood attribute value group—(NAG)—a collection of wafer element attribute values of each wafer element within the neighborhood pattern. The invention provides a defect detection system that has (i) a light source and an optical system for directing and focusing a light beam to impinge upon a wafer element, (ii) multiple detectors that are spaced apart from each other but concurrently directed at the wafer element as to provide a DSS, (iii) a processor for receiving the DSS and for processing it to indicate whether the wafer element is defective, (iv) a scanning mechanism for scanning the wafer with the light beam. It is noted that the scanning mechanism may include optical deflectors, mechanical stages and other elements that introduce a relative movement between the wafer and the light beam.

According to an aspect of the invention, at least one attribute operator is applied to at least two DSs arising from a given wafer element to provide at least one attribute value assigned to that wafer element. The attribute operations are defined to achieve at least one of the following goals: noise reduction, false alarm ratio reduction, improved sensitivity, improved signal to noise ratio, and the like.

The determination of the attribute operations may be responsive to various parameters such as the layer that is to be inspected, the manufacturing phase or stage of the inspected surface that precedes the defect inspection process, the estimated characteristics of the inspected object substrate, the estimated characteristics of defects to be found, the detectors configuration and the like.

The determination may be also responsive to the scattering patterns from the inspected wafer itself, such as scattering patterns from periodical patterns.

It has been shown that various wafer patterns and even various defects, such as scratches, rough surfaces, crystal defects, foreign particles, and even subsurface abnormalities are characterized by their scattering patterns. These scattering patterns may be either calculated by implementing well known mathematical models or may be obtained by measurements. The selection of attribute operation may be responsive to these scattering patterns and especially to the light gathered by the multiple detectors in response to a generation of such scattering patterns, as the detectors sample the scattering patterns.

According to another aspect of the invention the defect detection-system is also operable to obtain and process NDGs.

According to yet a further aspect of the invention the detect detection process includes a step of typing. The typing of AV obtained from applying a certain attribute operator may be responsive to AV obtained by applying another attribute operator of from a combination of other attribute operators.

According to yet a further aspect of the invention the DSS is split to two portions—a first portion is used for typing while the other portion is processed in response to that typing. The first portion may result from bright field detectors while the second portion may result from dark field detectors and vice verse, but this is not necessarily so. It is noted that signals obtained from bright field detectors may be utilized to define the matter from which a defect is made and accordingly to define the type of wafer element attribute value.

It is noted that in many cases the neighborhood pattern of a certain wafer element is symmetrical around that certain wafer element and has a rectangular shape, but this is not necessarily so. The wafer element neighborhood detection signals are processed to determine the thresholds applied in the comparison of inspected and reference wafer element attribute values, to indicate whether the wafer element is defective. For example, a typical neighborhood pattern may include ((5×5)−1) wafer elements. When utilizing six detectors, each DSS includes six DSs while each NDG includes ((5×5)−1) NSSs, each including six NS associated to the same neighborhood wafer element.

Usually, the neighborhood pattern includes much more than two wafer elements. After wafer element detection signals of a certain wafer element are generated their values are stored in a memory unit to be later used whenever that certain wafer element is within a neighborhood pattern of other wafer elements.

Additional advantages of the present invention will become readily apparent to those skilled in this art from the following detailed description, wherein only the embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DESCRIPTION OF THE INVENTION

Figure 1:
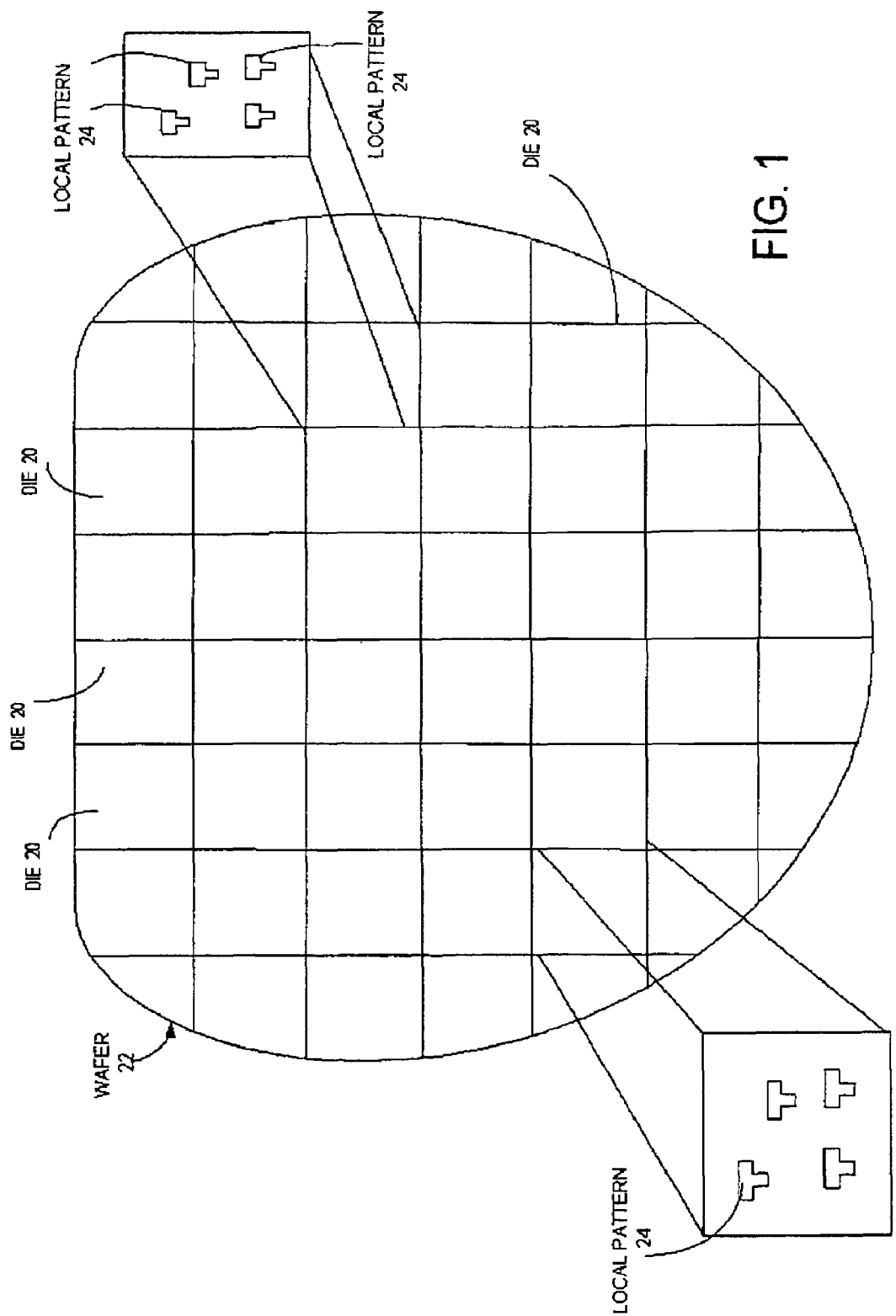
FIG. 1 illustrates a wafer to be inspected by the method for defect detection, in accordance with an embodiment of the invention.

Referring to FIG. 1, an article to be inspected, such as a semiconductor wafer 22, is processed (prior to inspection) to have a plurality of ideally identical patterned integrated circuit dies 20, each die 20 having comparable patterns, such as the T-shaped patterns 24 formed on the surface of wafer 22. It is noted that a single die may include a large amount of patterns that exceed millions of patterns per die. A semiconductor die usually includes a plurality of layers. A pattern, such as local pattern 24 may be a part of a metal interconnection line, a trench, a via, a conductive gate, etc.

Figure 2:
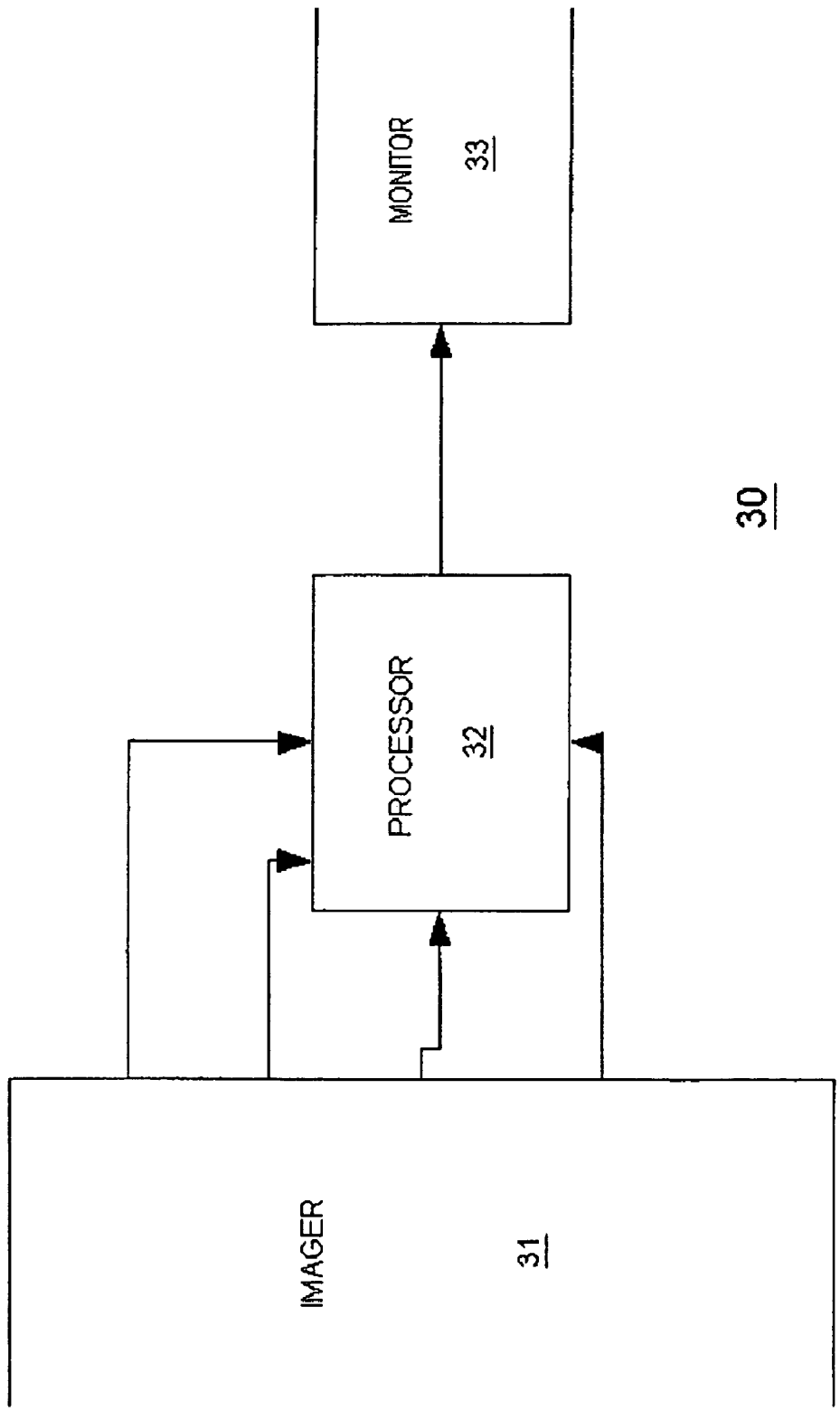
FIG. 2 illustrates a system for defect detection and for obtaining pixels, in accordance with an embodiment of the invention.

Referring to FIG. 2, illustrating a defect detection system 30 that includes: (i) light source 31 and an optical system 33 for directing and focusing a light beam to impinge upon a wafer element, (ii) multiple detectors, such as detectors 41-48 of FIG. 3*a* or detectors 41, 43, 45, and 47 of FIG. 3*b*, whereas the multiple detectors provide a DSS for each illuminated wafer element. Each detector is operable to receive light signals resulting from an interaction between the light beam and the wafer element, and to provide a DS. The multiple detectors are positioned as to receive light signals from at least two directions, (iii) processor 32 for receiving, for each wafer element the associated DSS for processing the DSS and (iv) a scanning mechanism 34 for scanning the wafer with the light beam. It is noted that the scanning mechanism may include optical deflectors, such as acousto-optic deflectors, galvanometric scanning mirrors, and/or mechanical stages and other elements that introduce a relative movement between the wafer and the light beam.

According to another aspect of the invention processor 32 is further operable to determine a presence of a defect in response to at least a portion of the wafer element NDG.

According to yet a further aspect of the invention processor 32 is operable to determine a presence of a defect in response to a combination of at least a portion of the wafer element DSS and at least a portion of the wafer element NDG.

The defect detection method can be implemented by various detection tools, as means and methods for obtaining wafer element detection signals are known in the art. The detection tools may have multiple detectors that include at least one dark field detector and/or at least one bright field detector. The detectors may have the same characteristics (such as sensitivity, gain, dynamic range), but this is not necessarily so. The wafer element detection signals may be obtained by the Alumot system but other multi-detector systems having other arrangement of detectors may be utilized for obtaining detection values.

It is noted that the detectors may be responsive to distinct polarizations and/or to distinct wavelengths. For example, a first detector may be responsive to horizontally polarized green light while a second detector is responsive to circular polarized red light. The first and second detector may be responsive to light from distinct directions, but this is not necessarily so. It is noted that the wavelength/polarization response may be determined by the detector itself or by filters that are characterized by wavelength/polarization. It is further noted that the detectors may be located at different elevations in relation to the wafer. In many cases the relationship (ratio, difference and the like) between signals from detectors at different elevations is a useful attribute operation that can also be utilized for typing.

Figure 3A:
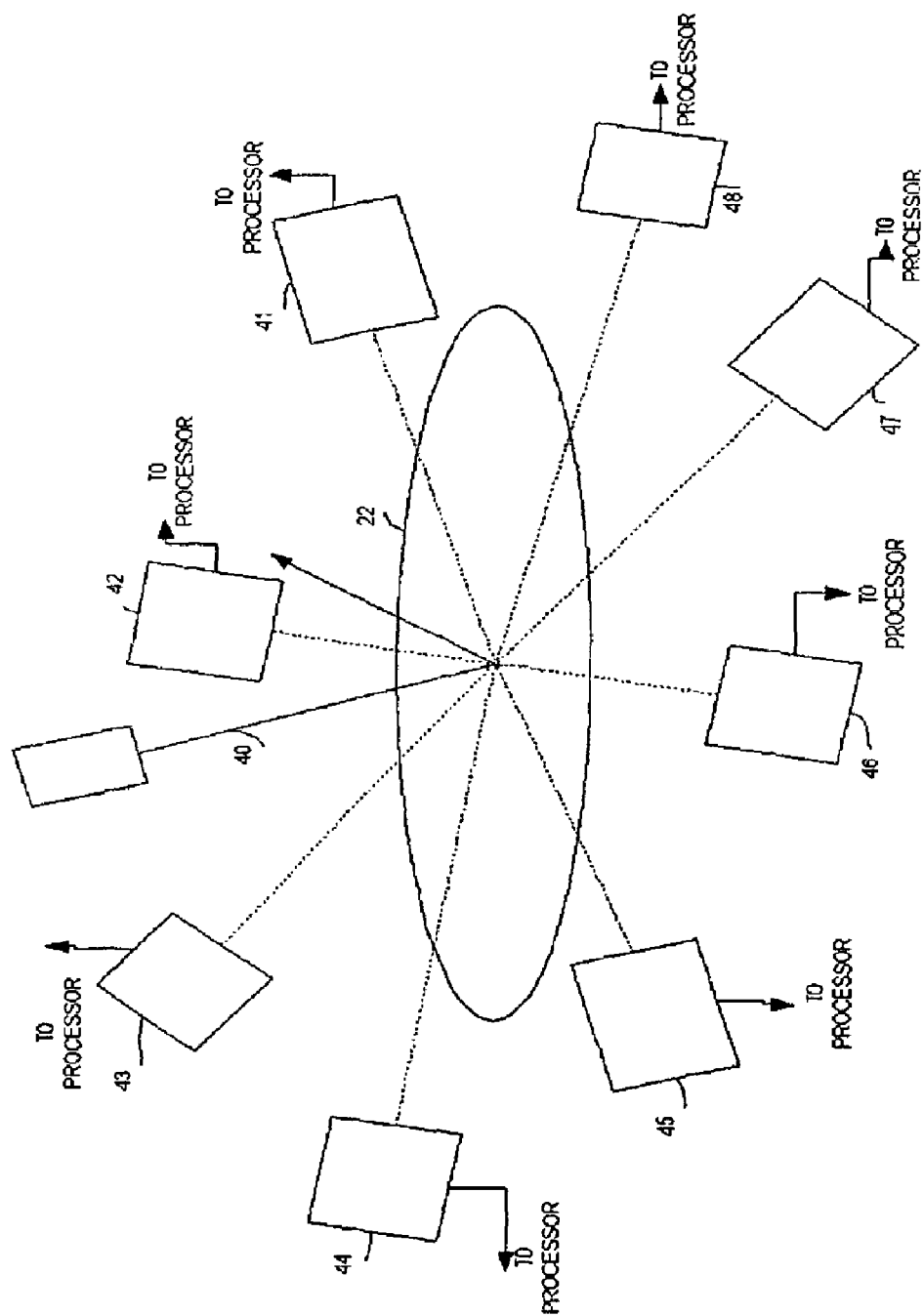
FIGS. 3a and 3b illustrate portions of the system of FIG. 2, in accordance with embodiments of the invention.

Referring to FIG. 3*a*, illustrating an arrangement of detectors of imager 31, in accordance with an embodiment of the invention. An vertical light beam 40 is directed onto a horizontally displaced wafer 22. Eight detectors, such as detectors 41-48 are arranged spatially away from the normal reflection direction (i.e., Snell's Law reflection) of light beam 40. Thus, the eight detectors 41-48 provide dark field images from eight perspectives in the form of continuous data streams. Another detector (not shown) may be positioned such as to receive a specularly reflected beam, thus providing a bright field image of the scanned wafer. The bright field detector may be a point sensor or an array of light sensors, such as a CCD. The eight detectors are positioned such to receive light scattered at light collecting zones that are located at the following angles (measured at the x-y plane): 22.5°, 67.5°, 112.5°, 167.5°, 202.5°, 257.5°, 292.5° and 337.5°

Figure 3B:
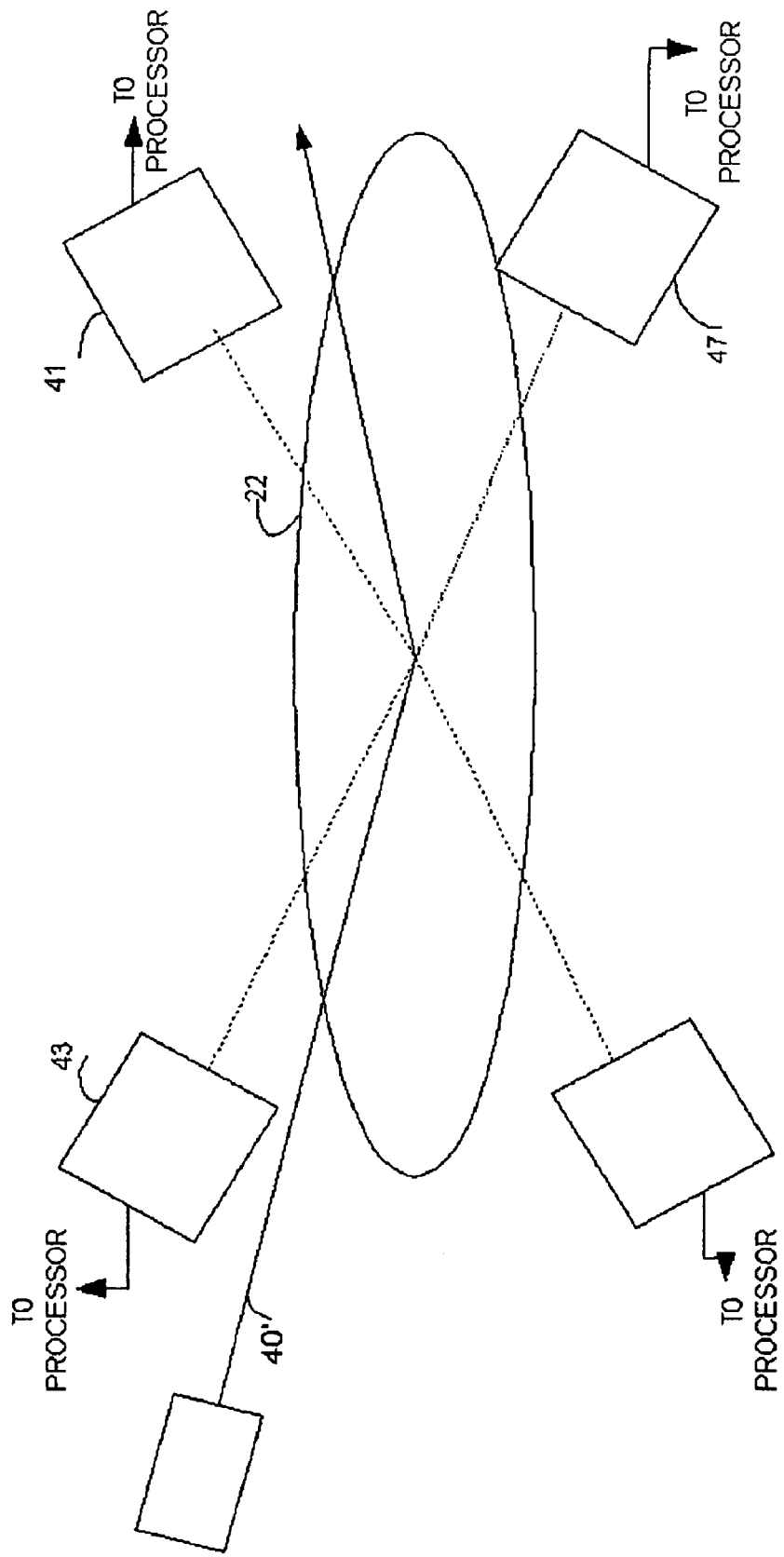

Referring to FIG. 3*b*, illustrating an arrangement of detectors of imager 31, in accordance with another embodiment of the invention, a light beam 40' is directed at a grazing angle onto a horizontally displaced wafer 22. Four detectors, such as detectors 41, 43, 45 and 47 are arranged spatially away from the normal reflection direction (i.e., Snell's Law reflection) of light beam 40'. Thus, the four detectors 41, 43, 45 and 47 provide dark field images from four perspectives in the form of continuous data streams. Another detector (not shown) may be positioned such as to receive a specularly reflected beam, thus providing a bright field image of the scanned wafer. The bright field detector may be a point sensor or an array of light sensors, such as a CCD. The four detectors are positioned such to receive light scattered at light collecting zones that are located at the following angles (measured at the x-y plane): 45°, 135°, 225° and 315°.

Figure 4:
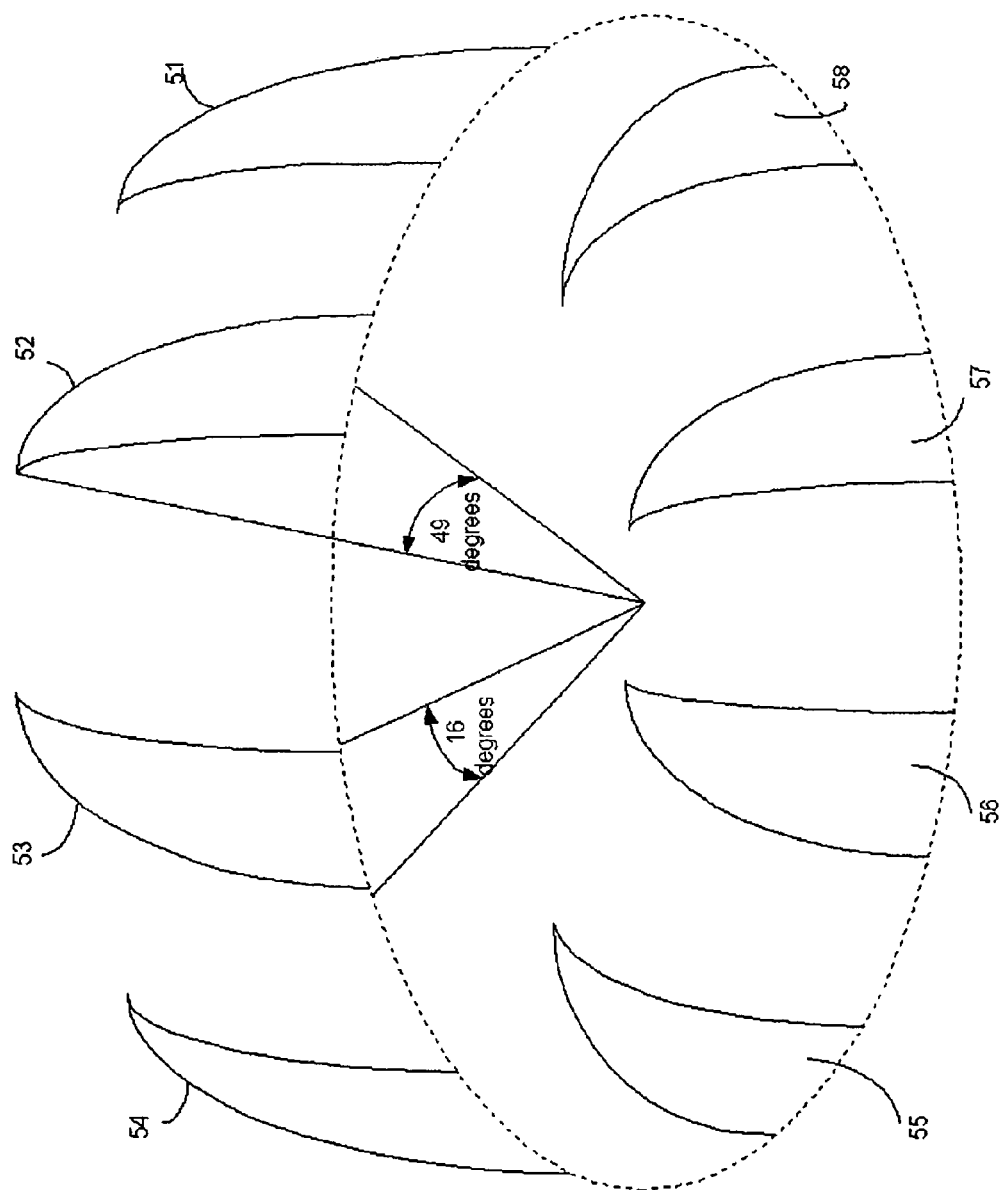
FIGS. 4-5 illustrate light collection zones of the portions of FIGS. 3a-3b, in accordance with various embodiments of the invention.

Referring to FIG. 4 illustrating the light collecting zones 51-58 of detectors 41-48 of FIG. 3*a*. It is noted that FIG. 4 illustrates identical non-overlapping light collecting zones, that have the same elevation, but this is not necessarily so. The detectors may have different light collecting zones, at least some light collecting zones may be located at different elevations in relation to the wafer surface and the light collecting zones may partially overlap. It is also noted that the distances between each pair of adjacent light collecting zones is the same, but it also not necessarily so. Furthermore, the detectors may have light collecting zones of distinct shape. For convenience of explanation is assumed that a direction is defined by a light collecting zone, thus light scattered and collected by two distinct and not fully overlapping light collection zones are considered as light collected from two distinct directions.

FIG. 4 illustrates eight light collecting zones 51-58 of detectors 41-48 respectively, the width of each light collecting zone is 16 degrees at its bottom surface and is substantially zero at its top, its height is 49 degrees. The light collecting zones are located such as to reduce the collection of light from the patterns of the wafer. Often the pattern is defined by lines. Most of these lines are oriented at 0°, 90°, 180° and 270°, while some lines are oriented at 45°, 135°, 225° and 315°. Accordingly, the light collecting zones are located to collect the light at the midway regions between these angles, such as 22.5°, 67.5°, 112.5°, 167.5°, 202.5°, 257.5°, 292.5° and 337.5°. The eight light collecting zones provide eight samples (eight wafer element detection signals) of each scattering pattern resulting from an interaction between a light beam and a wafer element.

Figure 5:
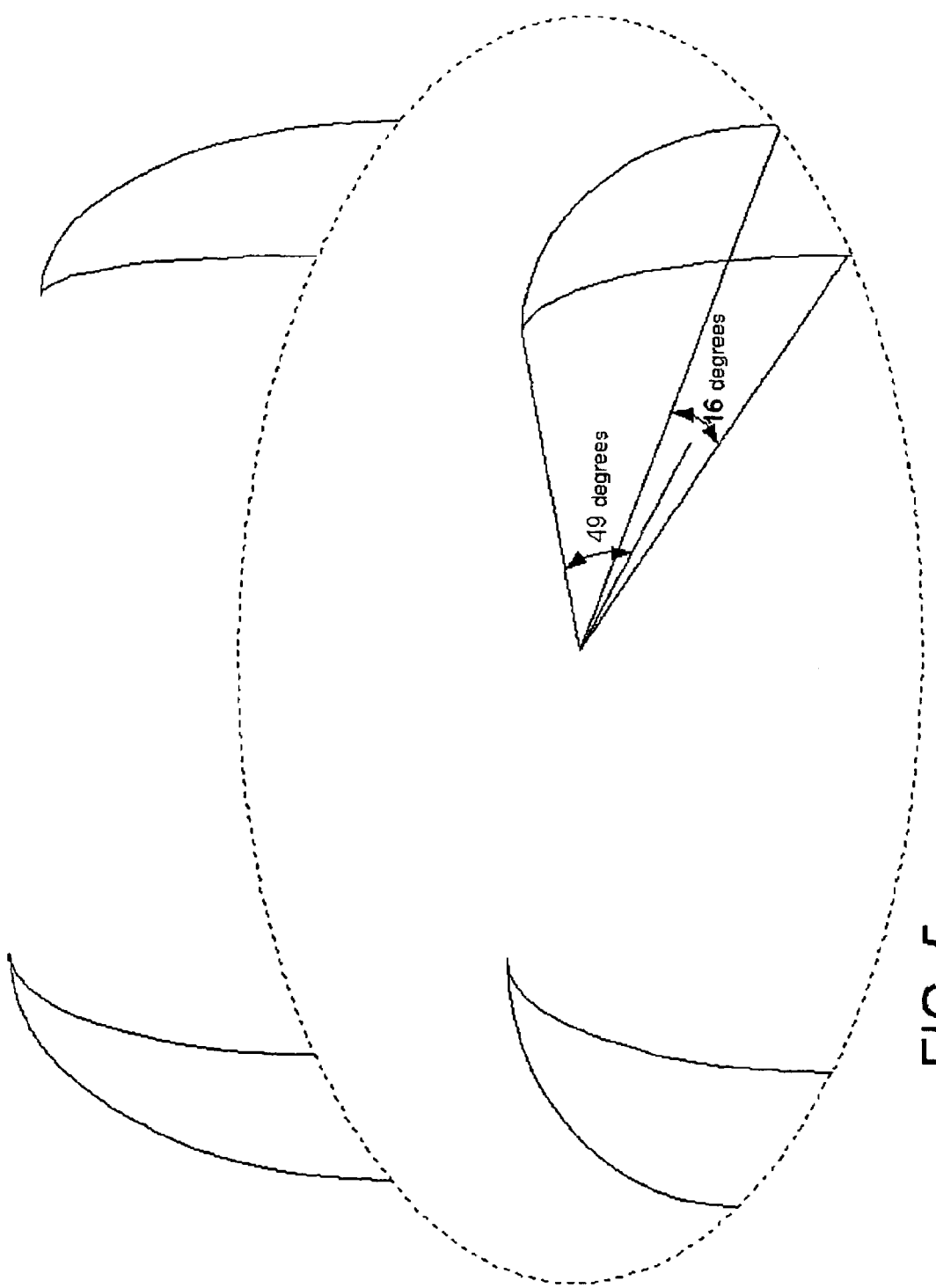

FIG. 5 illustrates four light collecting zones 51, 53, 55, and 57 of detectors 41, 43, 45 and 47 of a FIG. 3*b*. The width of each light collecting zone is 16 degrees at its bottom surface and is substantially zero at its top, its height is 49 degrees. The light collecting zones are located such as to reduce the collection of light from the patterns of the wafer. Usually, the pattern is defined by lines. Most of these lines are oriented at 0°, 90°, 180° and 270°. Accordingly, the four light collecting zones are located at 45°, 135°, 225° and 315° to collect the light at the midway regions between some of these angles. The four light collecting zones provide four samples (four wafer element detection signals, each wafer element detection signal representative of the aggregate intensity of light signals that are scattered within the respective light collecting zone) of each scattering pattern resulting from an interaction between a light beam and a wafer element.

For example, assuming that a foreign particle has a relatively symmetrical scattering pattern, and that each detector has the same characteristics (including the same gain) then each detector out of detectors 41, 43, 45 and 47 shall detect substantially the same amount of light and produce almost the same detection signal.

Yet a further example, assuming that a scattering pattern of a long and narrow scratch oriented at 30° to the x-axis (the wafer being located at the x-y plane) is characterized by a strong 30° and 210° lobes and weak 120° and 280° lobes, and that each detector has the same characteristics (including the same gain), then detectors 41 and 45 do not receive the peak of these lobes but receive the strongest light intensity signals, while detectors 43 and 47 receive the weakest light signals.

Figure 6:
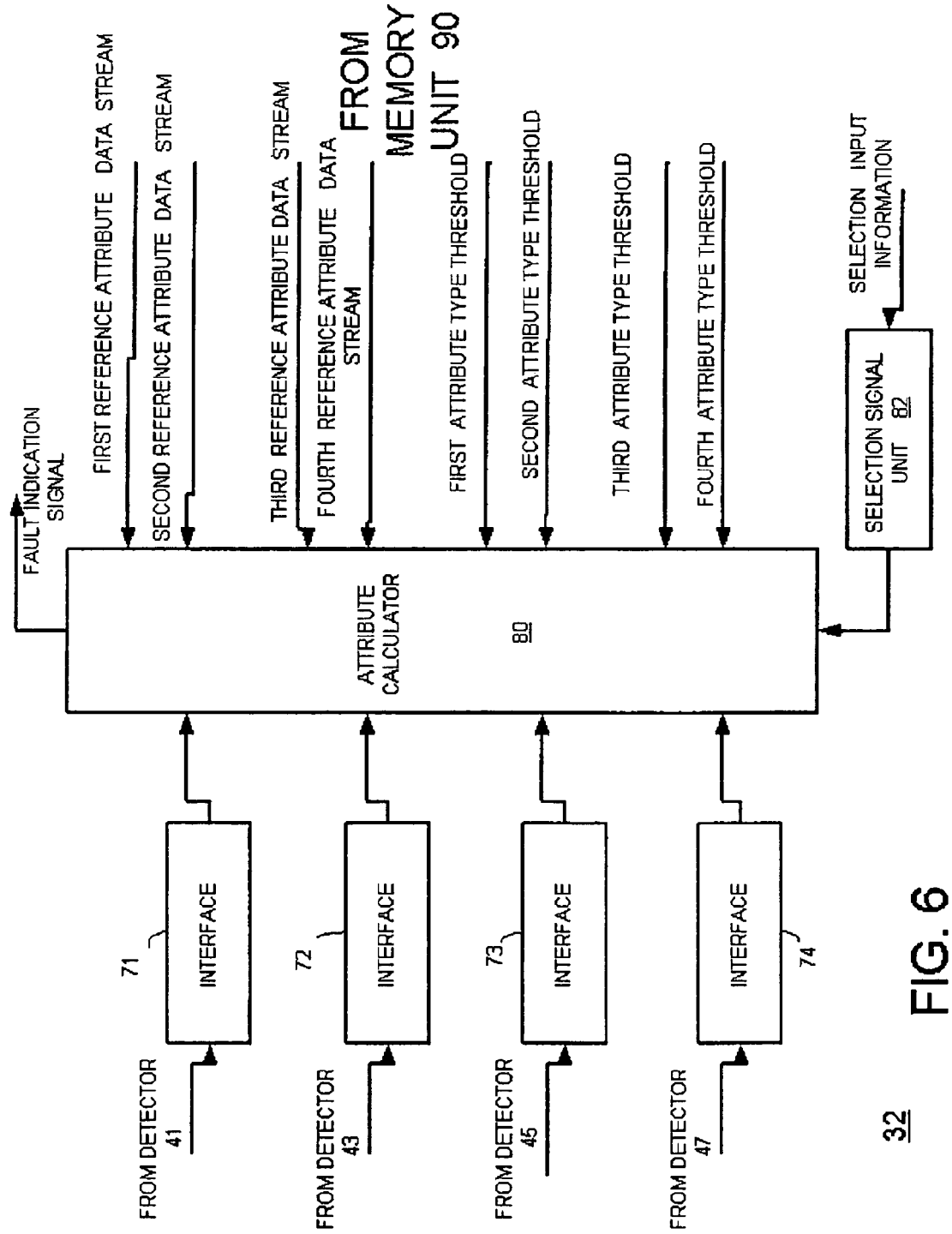
FIG. 6 illustrates a first portion of processor in accordance with an embodiment of the invention.

FIG. 6 illustrates a portion 320 of processor 32 in accordance with an embodiment of the invention. Processor 32 may also include additional portions (not shown) for performing phase II calculations. Portion 320 is coupled to memory unit 90 and is operable to receive and process data streams provided from multiple detectors. For convenience of explanation it is assumed that processor 32 is operable to process wafer element detection signals from four detectors, such as detectors 41, 43, 45 and 47 of FIG. 3*b*.

Processor 32 has four interfaces 71-74 for receiving data streams from four detectors 41, 43, 45 and 47 and is also coupled to multiple data buses for receiving reference attribute data streams and thresholds from memory unit 90. If detectors 41, 43, 45 and 47 provide an analog signal, then interfaces 71-74 sample the analog signals at a predefined rate to provide digital signals.

The four digital data streams are provided to attribute calculator 80 that generates at least one attribute data stream in response to the reception of the four digital data streams. For convenience of explanation it is assumed that attribute calculator 80 generates four attribute data streams and that each attribute data stream is a different function of the four digital data streams provided by interfaces 71-74, but this is not necessarily so. Attribute calculator 80 may also receive a selection signal from selection signal unit 82 for selecting which attribute operation to apply and which attribute data streams to provide. Selection signal unit receives selection information such as current location of the inspecting light beam, characteristics of the currently inspected surface (such as surface material), stage of the inspected die manufacturing, and the like.

Processor 32 may be operable to execute die-to-die, and/or die-to-database defect detection schemes. For convenience of explanation it is assumed that processor 32 executes a die-to-die defect detection scheme. In this scheme inspected attribute data streams that are currently generated as a result of a current interaction between a light beam and the substrate of the inspected object are compared to previously generated reference attribute data streams. It is noted that in a die to die defect detection scheme the inspected attribute data streams may be compared to another currently generated reference attribute data streams. The reference attribute data streams are generated as a result of an interaction between another light beam and the inspected object.

Each inspected attribute data stream is compared to a corresponding reference attribute data stream and to an attribute threshold corresponding to the attribute data streams. An inspected attribute data stream and a reference attribute data stream correspond if (i) they were generated by the same attribute operator, and (ii) the attribute operator was applied to detection values that arise from the same relative location on the reference die and the inspected die. It is noted that when implementing pattern to pattern cell-to-cell comparisons the location is relative to the cell whereas each wafer includes multiple cells, and a cell to cell comparison may involve a comparison of two cells of the same wafer that ideally have the same patterns.

The results of the comparisons between the inspected attribute data streams and reference attribute data streams indicate whether or not a wafer element is suspected of being defective. The wafer element will be suspected as being defective if the difference between the inspected and reference attribute values is above the threshold.

The attribute operations are defined to achieve at least one of the following goals: noise reduction, false alarm ratio reduction, improved sensitivity, improved signal to noise ratio, and the like. The determination of the attribute operations may be responsive to various parameters such as the layer that is to be inspected, the manufacturing phase or stage of the inspected surface that precedes the defect inspection process, the estimated characteristics of the inspected object substrate, the estimated characteristics of defects to be found, the detectors configuration and the like. The determination may be also responsive to the scattering patterns from the semiconductor itself, such as scattering patterns from periodical patterns.

For example, it is known that back-end layers (such as metal layers) of multi-layer semiconductors are much more noisy than front-end layers (such as poly-silicon layers). It is noted that multi-layered semiconductors are manufactured by a multi-staged manufacturing process, starting from the manufacturing of bare wafers and front-end layers and usually ending at the manufacturing of back-end layers. While front-end layers include components such as transistors, diodes and the like the metal layers provide connectivity between the components. Furthermore, metal layers are commonly characterized by multiple grains that are polycrystalline regions of different crystallographic orientation. The scattering pattern from a grain often consists of two strong lobes directed oppositely in azimuth.

Accordingly, attribute operations that intensify the detection signals from the detectors may be selected in relatively quiet environment, such as front-end layers. This kind of detection may be implemented during an early manufacturing stage of the multi-layer semiconductor substrate. On the other hand, attribute operations that reduce noise or attribute operations that combine signals that arrive from adjacent detection channels may be selected when back-end layers are detected for defects. This kind of detection may be implemented during a late manufacturing stage of the multi-layer semiconductor substrate.

The following equations illustrate six exemplary attribute operations that may be applied by attribute calculator 80:

$$AT_1 = 0.25 \times (P_{41} + P_{43} + P_{45} + P_{47}) \qquad (i)$$

$$AT_2 = \sqrt{(P_{41} \times P_{45} \times P_{43} \times P_{47})/2} . \qquad (ii)$$

$$AT_3 = \sqrt{(P_{41} \times P_{43} \times P_{45} \times P_{47})/2} . \qquad (iii)$$

$$AT_4 = MAX(P_{41}, P_{43}, P_{45}, P_{47}) \qquad (iv)$$

$$AT_5 = 0.5 \times MAX(P_{41} + P_{43}, P_{45} + P_{47}). \qquad (v)$$

$$AT_6 = 0.5 \times MAX(P_{41} + P_{45}, P_{43} + P_{47}). \qquad (vi)$$

AT means an attribute operator value, $P_{41}$, $P_{43}$, $P_{45}$, $P_{47}$ are the output signal values of detectors 41, 43, 45 and 47 respectively. MAX denotes the operation of selecting the greatest element out of a set of elements. It is noted that each output signal ($P_{41}$, $P_{43}$, $P_{45}$, $P_{47}$) may be further multiplied by a weight factor. The weight factor may be either predefined or determined in response to a previous defect detection process that is being applied to semiconductor wafers, or in response to the detectors characteristics such as sensitivity and gain.

It is noted that according to an aspect of the invention the defect determination process is based upon wafer neighborhood attribute values. The amount of wafer neighborhood attribute values is directly proportional to the amount of pixels within the neighborhood pattern. Usually, larger neighborhood patterns require either additional computational and storage resources or may eventually limit the complexity of the attribute operators to comply with the system throughput requirements.

The first attribute operator (first equation) reduces random noise signals as the noise signals are averaged out. The second attribute operator amplifies scattering patterns such as those that are produced from an interaction of light with a scratch. The third attribute operator (third equation) is useful for reducing signals from grains or lines having relatively strong lobes directed towards two opposite detectors and relatively low lobes directed towards the two other detectors.

Figure 7:
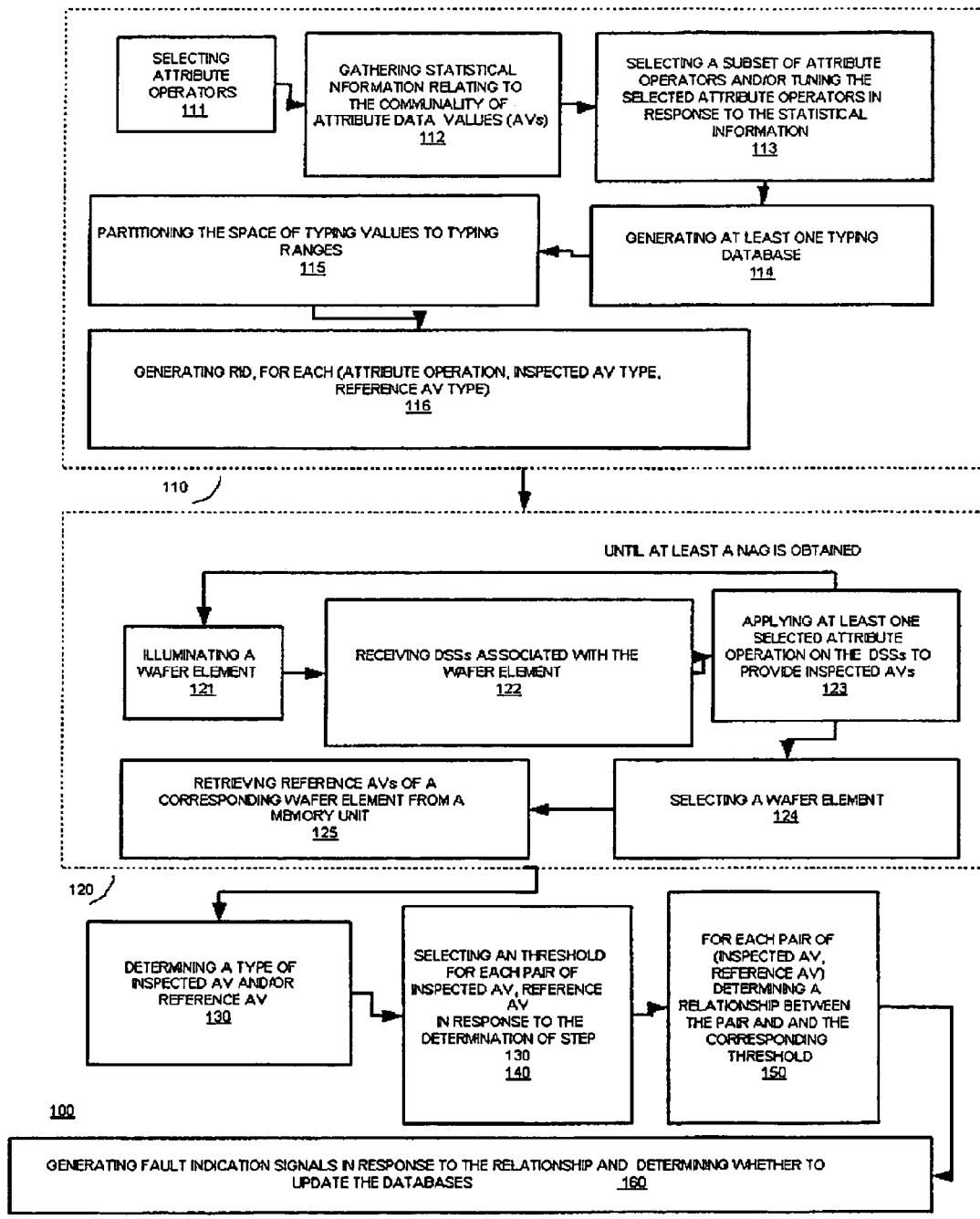
FIGS. 7-8 are flow charts illustrating methods for defect detection, in accordance with various embodiments of the invention.

FIG. 7 illustrates method 100 for inspecting a substrate for defects, in accordance with an embodiment of the invention. Method 100 determines whether a wafer element is defective in response to the DSS of that wafer element. Method 100 starts by initialization step 110. Step 110 may include step 111 of determining which attribute operators to select, and even determining how to tune the selected attribute operators. The selection may be responsive to data relating to the substrate which is about to be examined, to the stage in the manufacturing process in which the defect detection method is about to be implemented, to knowledge of previously detected defects, to data relating to the manufacturing process and especially to probable malfunctions, a design rule data base, CAD design tools, or previous iterations of the defect detection method.

Step 111 is followed by step 112 of gathering statistical information relating to the communality of AVs. A plurality of dies may be inspected to build a statistically significant sample population, in a manner known to those skilled in the art.

According to an aspect of the invention, step 112 may be followed by step 113 of selecting a sub-set of the selected attribute operations or either adjusting or tuning the selected attribute operations in response to the statistical information gathered during step 111. The additional selection or tuning is aimed to provide attribute operations that obtain at least one of the following goals: higher signal to noise ratio, lower false alarm level, better sensitivity and the like.

Step 110 also includes various steps involving "typing". Typing allows for applying distinct defect decision rules (such as applying different threshold curves) to distinct wafer elements types. This "typing" is initialized at steps 114-116.

It is noted that AVs obtained by applying a certain attribute operator to certain DSs are assigned a type according to values that are not obtained by applying that certain attribute operator to those certain DSs.

According to an aspect of the invention each AV may be typed according to values obtained by applying a combination of other attribute operations.

According to yet another aspect of the invention, typing values may be obtained by applying a certain attribute operator to various DSs of the same DSS, while these typing values are utilized to type attribute values obtained by applying the same certain attribute operator to other DSs.

It is further noted that the typing attribute operations may be applied to DS and/or NS that form portions of a DSS and/or a NAG respectively.

For convenience of explanation it is assumed that a dedicated attribute operator is utilized for typing. That attribute operator is referred to as typing attribute operator. The values obtained by the application of the typing attribute operator are referred to as typing values.

Step 114 includes generating a typing database. The typing database reflects the frequency of occurrence of typing values. The typing database may be graphically illustrated by a curve. It is noted that each attribute operator out of the selected attribute operators may have its own typing database.

Step 114 is followed by step 115 in which the space of typing values is partitioned to typing ranges. The selection is conveniently responsive to the distribution of the typing values, as may be graphically illustrated by a curve that links between typing attribute values and their appearance. Conveniently, adjacent typing ranges are delimited by borders that are located at local minima of that curve. Locating the borders at the local minima reduces the amount of erroneous typing, as each border is surrounded by relatively less common typing values.

It is noted that the allocation of typing ranges can also be responsive to the amount of data points (of typing values) within each typing range, to a location of local maxima and even local maxima that are above a predefined significance threshold, such as to assure that each typing range includes a significant amount of data points. Step 115 can also include allocating the typing ranges in response to inputs provided by an end-user, thus allowing for tailoring the method to end-users requirements.

When more than a single typing database is utilized for typing the amount of typing ranges and their partition may vary from typing database to another.

Step 115 is followed by step 116 of generating, for each attribute operation and for each type, a reference/inspected attribute/type database (RID) reflecting the frequency of occurrence of pairs of (inspected AV, reference AV) of wafer elements attribute values that belong to that attribute and type. This type may be responsive to the inspected AV type and reference AV type. For example, if there are H distinct attribute operators, and each attribute operator is associated with T distinct type, there may be up to (H×T×T) RIDs. According to another aspect of the invention the type of both inspected AV and reference AV is determined by a selected type. In such a case there may be only (H×T) RIDs. The selected type may be selected in accordance to patent application titled "Method for detecting defects" of Levin et al., filed at Nov. 28 2001 that is herein incorporated by reference.

A RID may be graphically illustrated by a three-dimensional graph, whereas the x-y plane illustrates pair of (inspected wafer element attribute value, reference wafer element attribute value), while the z-axis illustrates the amount of pairs that have the same value. Step 116 further includes defining a two dimensional RID envelope, for each attribute and for each type, and defining a threshold, for each attribute and for each type. This threshold is referred to as an attribute/type threshold.

Each RID envelope is selected such as to include a predefined amount of pairs, or to guarantee a predefined maximal amount of false alarms. For example, the RID envelope may be selected to surround pairs of (inspected wafer element attribute value, reference wafer element attribute value) within up to six standard deviations from the mean of data points that form the RID.

Thresholds may be selected in accordance with various criteria. A threshold is usually an estimation of a more complex curve that surrounds all those pairs that comply with a predefined statistical criterion. The estimation is done in view of timing and computational limits as well as accuracy and false alarm rates. For example, a first threshold may be a line that is tangent to the RID's envelope. Another threshold may include three line segments that approximate the RID's envelope; the three segments are located slightly above the RID's envelope. Another threshold may be a line that is substantially parallel to the mean of data points that form the RID. Yet a further threshold is line that is located at a predetermined distance from the RID's envelope. It is noted that other thresholds may be selected, such as threshold that includes a line that reflects data points that are located within a pre-defined statistical parameter from the mean of data points that form the histogram.

According to an aspect of the invention the location of a pair of inspected wafer element attribute value and reference wafer element attribute value, is compared to a location of a threshold to provide an indication about the presence of a defect. According to another aspect the amount of pairs that are located outside the RID's envelope is also taken into account.

Step 110 is followed by step 120 of obtaining inspected AVs and reference AVs. The inspected AVs can be obtained by various detection systems, such as but not limited to the systems of FIGS. 2 and 3. Reference AVs are usually obtained from a storage unit, but they can also be obtained by the detection system itself.

Step 120 usually includes the following steps:

Step 121 of illuminating a wafer element, for example by vertical light beam 40 of FIG. 3.

Step 122 of receiving a DSS associated with that wafer element.

Step 123 of applying the selected attribute operations to provide inspected AVs.

It is noted that steps 121-123 may be repeated until multiple AVs, associated with multiple wafer elements on the inspected die are generated and temporarily stored. According to an aspect of the invention steps 121-123 may be repeated until a NAG is obtained. According to yet a further aspect of the invention steps 121-123 are repeated until each wafer element of at least one pre-defined block are illuminated and the corresponding wafer element attribute values are calculated and stored.

(D) Step 124 of selecting a wafer element (out of the at least one block) thus defining an inspected wafer element having inspected AVs. The selection may follow a predefined pattern, such as a raster scan pattern, but other selection schemes may be implemented. Usually, the predefined pattern includes contiguous wafer elements, but this is not necessarily so. It is noted that when a single iteration of steps 121-123 is executed, step 123 is followed by step 125, as there is no need for selecting an AV out of a grid of AVs.

(E) Step 125 of retrieving reference AVs out of a storage unit. It is noted that step 120 usually includes an alignment step such that the inspected AVs and the reference AVs relate to nominally identical wafer elements. Nominally identical wafer elements may be located at the same location on the inspected die and reference die, or to the same location on different patterns on the same die, respectively. Alignments are usually made in the wafer element domain, but this is not necessarily so. Alignment methods are known in the art. An illustration of a method for such an alignment is described in U.S. Pat. Nos. 5,699,447, 5,982,921 and 6,178,257B1 of Alumot, which are hereby incorporated by reference. Another alignment method is described at U.S. Pat. No. 5,659,172 of Wagner, which is hereby incorporated by reference.

Step 120 is followed by step 130 of determining a type, for each application of an attribute operation to at least one DS. For each attribute operation that is applied to at least one DS the type determination is responsive to the result of the application of the typing function to the at least one DS. The type is determined by the range in which the result is included. It is noted that distinct attribute operators may be associated with different typing functions. Step 130 is followed by step 140 of selecting a threshold (defined during step 115), for each inspected AV, in response to the type associated with the AV's attribute operation.

Step 140 is followed by step 150 of determining a relationship, for each inspected AV, between the corresponding threshold, the inspected AV and the corresponding reference AV to indicate the presence of a defect.

Step 150 involves determining the location of a pair of (inspected AV, reference AV) that are characterized by an attribute operator and type, in relation to the threshold of that attribute operator and type. If no defect is detected step 150 is followed by step 120, else step 150 is followed by step 160 of evaluating the distance between the pair (inspected AV, reference AV) and the attribute type threshold. The probability of a presence of a defect is usually proportional to this distance, although the length can also be responsive to a characteristic of the defect (for example, the material from which a foreign particle is made and the like).

Step 160 also includes generating a fault indication signal. The fault indication signal can be utilized by defect review devices, such as phase II of the Alumot system.

Step 160 may also include determining whether to update databases such as RIDs, typing databases and the like, and performing the update. The databases are usually updated only when a defect was not detected—only when the fault indication signal is below a predefined threshold. This update is usually done off-line, after further inspection of the wafer and even after phase II processing is accomplished. The database updates may result in a threshold update, but this is not necessarily so.

Figure 8:
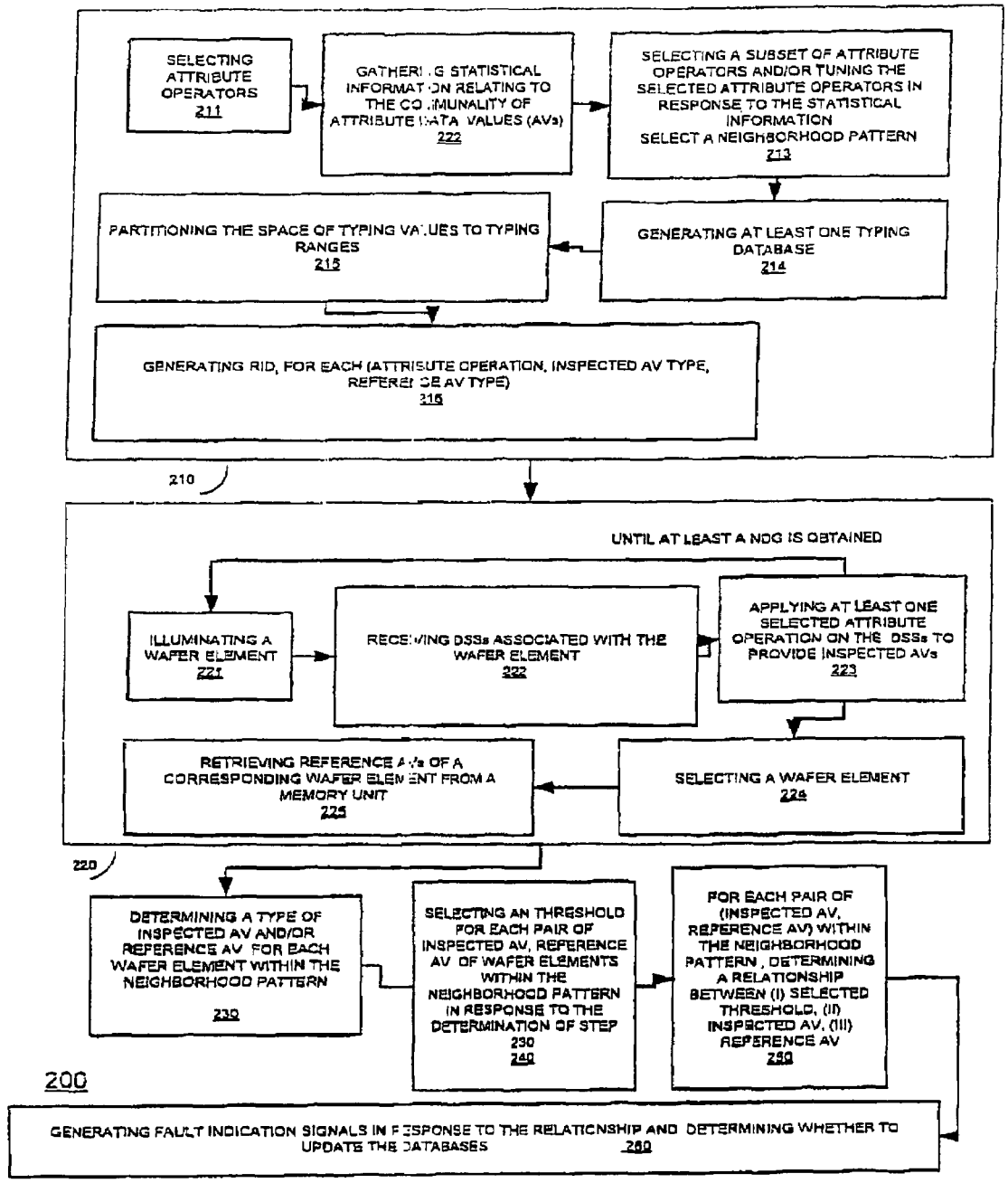

FIG. 8 illustrates method 200 for inspecting a substrate for defects, in accordance with an embodiment of the invention. Method 200 resembles method 100 but determines whether a wafer element is defective in response to the DSS of that wafer element and at least a portion of the NDG of that wafer element. Accordingly, attribute operators are applied to portions of NSS and not just to portions of the DSS of a wafer element. Alternatively, attribute operations may be applied to both a portion of NSS and a portion of DSS. The AV generated by the application of the attribute operations are processed to determine whether a defect exists, the nature of the defect and even the probability of such a defect.

It is noted that method 100 applied attribute functions that were able to convert multiple DSs to a single AV. As method 200 is responsive to more detection signals (multiple NSs in addition to DSs), the attribute operators may be altered to provide a single AV for each wafer element. The larger amount of signals may also be handled by performing a preprocessing step on the detection signals (NS and optionally also DS) before applying the attribute functions, by applying a post-processing step after multiple AT per wafer element are provided (each relating to a wafer element out of the neighboring pattern).

To illustrate this point let assume that (i) a neighboring pattern includes 24 neighborhood wafer elements, (ii) the attribute operator of the first equation is applied, (iii) the defect detection process is based upon detection signals from six detectors, and (iv the defect detection process is responsive to the 24 NDs and to the six DSs.

Accordingly, applying the attribute operation of the first equation will result in twenty-five results, corresponding to each of the twenty-five wafer elements. These twenty five results can be converted to a single AV by applying a post-processing operation such as finding the average value of the twenty five results, finding a difference between the highest result and the lowest result, finding the highest or lowest result, and the like.

Method 200 starts by initialization step 210 that resembles step 110 but may further include a step of defining or selecting a neighborhood pattern and step of gathering statistical information relating to the frequency of occurrence of wafer element neighborhood attribute values and wafer element attribute values. Step 214 includes generating an attribute/type database, for each selected attribute operation. The attribute/type database of can be graphically illustrates by a histogram that reflects the statistical distribution of wafer element neighborhood attribute values associated with said attribute operator.

Step 110 also includes steps 214-216 that are analogues to steps 114-116.

Step 210 is followed by step 220 of obtaining inspected AVs, inspected NAGs, corresponding reference AVs and reference NAGs. The inspected AVs and NAGs can be obtained by various detection systems, such as but not limited to the systems of FIGS. 2 and 3. Reference NAGS and AVs are usually obtained from a storage unit, but they can also be obtained by the detection system itself.

Step 220 usually includes the following steps:

Step 221 of illuminating a certain wafer element, for example by vertical light beam 40 of FIG. 3.

Step 222 of receiving a DSS associated with that certain wafer element.

Step 223 of applying the selected attribute operations to provide inspected AVs.

For each wafer steps 221-223 are repeated until at least all neighboring wafer elements within the neighborhood pattern of the certain wafer element are illuminated and the detection signals that form the certain wafer element NDG are received and stored, and all NAGs are calculated. As in method 100, a predefined block of wafer elements, usually much larger than a neighborhood pattern of the certain wafer element, is illuminated and the corresponding wafer element attribute values are calculated and stored.

Step 223 is followed by steps 224 and 225 that resemble steps 124 and 125 of Method 100.

Step 220 is followed by step 230 of determining a type, for each attribute operation and for each wafer element within the neighborhood pattern. The determination is responsive to the location of typing values within typing ranges. If, for example, a single typing function is selected for all wafer elements within the neighborhood and each attribute operator then that typing operator is applied for each wafer element within the neighborhood pattern.

Step 230 is followed by step 240 of selecting a threshold, for each inspected wafer element in the neighborhood pattern and for each attribute operation, in response to the determination of step 220.

Step 240 is followed by step 250 of determining a relationship, for each inspected wafer element neighborhood attribute value, between the selected threshold, the inspected wafer element attribute value, and the corresponding reference wafer element attribute value, to indicate the presence of a defect. It is noted that the determination can also be responsive to the inspected wafer element neighborhood attribute value and the reference wafer element neighborhood attribute value. For example, comparing inspected wafer element attribute values to inspected wafer element neighborhood attribute values to provide a first difference value, then comparing reference wafer element attribute values to reference wafer element neighborhood attribute values to provide a second difference value and them comparing the first difference value to the second difference value.

Step 250 involves determining the location of multiple pairs of (inspected wafer neighborhood element neighborhood attribute value, reference wafer element neighborhood attribute value), a pair for each wafer element within the neighborhood pattern that are characterized by an attribute and type, in relation to the threshold of that attribute and type.

It is noted that step 250 may also include a postprocessing step that provides a single value that is responsive to the multiple values within the NDG. If no defect is detected step 250 is followed by step 220, else step 250 is followed by step 260 of evaluating the distance between the pair of (inspected wafer element neighborhood attribute value, reference wafer element neighborhood attribute value) and the attribute type threshold. The probability of the presence of a defect is usually proportional to this distance, although the length can also be responsive to a characteristic of the defect (for example, the material from which a foreign particle is made and the like).

Step 260 also includes generating a fault indication signal. The fault indication signal can be utilized by defect review devices, such as phase II of the Alumot system.

Step 260 may also include determining whether to update databases such as attribute/type databases, and performing the update. The databases are usually refreshed only when a defect was not detected—only when the fault indication signal is below a predefined threshold.

According to an aspect of the invention the selection of attribute operations may change during the defect detection of a single die or a single wafer. For example, a first set of attribute operation may be selected when inspecting bare portions of the wafer, another set may be selected when inspecting periodical patterns, such as arrays of memory cells, and yet a further set of attribute operators may be selected when inspecting non-periodical patterns such as logic cells. The selection is usually responsive to wafer element location information provided by the imaging system.

The present invention is applicable to the manufacture of various types of semiconductor devices, particularly high-density semiconductor devices having a design rule of about 0.18μ and under.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention could be practiced without resorting to the details specifically set forth. In other instances, well known processing structures have not been described in detail, in order not to unnecessarily obscure the present invention.

Only the embodiment of the present invention and but a few examples of its versatility are shown and described in the present disclosure. It is to be understood that the present invention is capable of use in various other combinations and environments and is capable of changes or modifications within the scope of the inventive concept as expressed herein.

We claim:

1. A method for inspecting a substrate for defects, the substrate comprising a plurality of elements, the method comprising the steps of:

for each element of the substrate, obtaining a detection signal set comprising a plurality of wafer element detection signals generated by a plurality of detectors, and a neighborhood detection signal group comprising a plurality of wafer element neighborhood signal sets, each wafer element neighborhood signal set comprising a plurality of wafer element neighborhood detection signals generated by the plurality of detectors for a wafer element within a neighborhood pattern of one of the substrate elements;

calculating for the detection signal set at least one wafer element attribute value;

calculating for each neighborhood detection signal set at least one wafer element neighborhood attribute value, to constitute a collection of wafer element neighborhood attribute values; and determining a relationship between the at least one wafer element attribute value, the collection of wafer element neighborhood attribute values, at least one threshold, at least one corresponding reference wafer element attribute value, and corresponding reference wafer element neighborhood attribute values, to indicate a presence of a defect;

wherein the at least one wafer element attribute value is calculated by applying one attribute operator on at least two of the wafer element detection signals belonging to the same detection signal set and generated from at least two of the detectors; and wherein the step of obtaining a wafer element detection signal set is preceded by a step of selecting a subset of attribute operations out of a set of attribute operators.

2. The method of claim 1 wherein a threshold is responsive to a wafer element attribute value.

3. The method of claim 1 wherein a threshold is responsive to a type of a reference wafer element attribute value.

4. The method of claim 1 wherein a threshold is responsive to a type of a wafer element attribute value and to a type of reference wafer element attribute value.

5. The method of claim 1 further comprising a step of building a typing database for each attribute operator.

6. The method of claim 1 wherein at least one of the wafer element detection signals are obtained in response to a reception of light of a predefined characteristic.

7. A method for inspecting a substrate for defects, the method comprising the steps of:

obtaining a set of first wafer element neighboring detection signals and a first wafer element detection signal from a first direction;

obtaining a set of second wafer element neighboring detection signals and a second wafer element detection signal from a second direction;

obtaining a set of third wafer element neighboring detection signals and a third wafer element detection signal from a third direction;

obtaining a set of fourth wafer element neighboring detection signals and a fourth wafer element detection signal from a fourth direction;

applying one attribute operator on at least two of the wafer element detection signals to provide at least one inspected wafer element attribute value;

applying the one attribute operator on the wafer element neighboring detection signals to provide a collection of neighboring wafer element attribute values;

obtaining at least one reference wafer element attribute value and at least one corresponding wafer element neighboring attribute value, each reference wafer element attribute corresponding to an inspected wafer element attribute; and determining a relationship between the at least one inspected wafer element attribute value, the at least one reference wafer element attribute value, the collection of neighboring wafer element attribute values, the at least one reference wafer element neighboring attribute value and at least one threshold to indicate a presence of a defect;

wherein the step of obtaining a first wafer element detection signal is preceded by a step of selecting a subset of attribute operations out of a set of attribute operators.

8. The method of claim 7 wherein at least one attribute operator is responsive to a maximal value of at least a pair of two obtained wafer element detection signals.

* * * * *